United States Patent [19]

Hill

[11] Patent Number: 4,925,798

[45] Date of Patent: May 15, 1990

[54] 3-HYDROXYDICARBOXYLIC ACIDS AND PROCESS FOR THEIR PRODUCTION

[75] Inventor: Frank F. Hill, Mettmann, Fed. Rep. of Germany

[73] Assignee: Huels Aktiengesellschaft, Marl, Fed. Rep. of Germany

[21] Appl. No.: 329,883

[22] Filed: Jan. 3, 1989

Related U.S. Application Data

[62] Division of Ser. No. 855,035, Apr. 23, 1986, Pat. No. 4,827,030.

[51] Int. Cl.$^5$ .......................... C12P 7/40; C12P 7/44; C12R 1/74
[52] U.S. Cl. .................... 435/136; 435/142; 435/924
[58] Field of Search .................. 435/136, 142, 924

[56] References Cited
PUBLICATIONS

Zutong et al., *Chem. Abstracts*, vol. 97(15), Oct. 11, 1982, p. 560, #125691k.
Hua et al., *Chem. Abstracts*, vol. 98(5), Jan. 31, 1983, p. 534, #33023m.
Ruishen et al., *Chem. Abstracts*, vol. 104(17), Apr. 28, 1986, p. 545, #147105n.
Tokuji et al., *Chem. Abstracts*, vol. 103(25), Dec. 23, 1985, p. 852, #214849c.

*Primary Examiner*—Ronald W. Griffin
*Assistant Examiner*—Pamela S. Webber
*Attorney, Agent, or Firm*—Millen, White & Zelano

[57] ABSTRACT

3-hydroxydicarboxylic acids of 12–18 carbon atoms are produced microbiologically from n-alkanes employing the yeast mutant *Candida tropicalis* DSM 3152.

6 Claims, No Drawings

3-HYDROXYDICARBOXYLIC ACIDS AND PROCESS FOR THEIR PRODUCTION

This is a division, of application Ser. No. 06/855,035 filed Apr. 23, 1986, now U.S. Pat. No. 4,827,030.

BACKGROUND OF THE INVENTION

This invention relates to straight chain, saturated 3-hydroxydicarboxylic acids and to the microorganism employed to produce them.

Short-chain 3-hydroxydicarboxylic acids are known. Thus, malic acid (n=0 in Formula I) occurs in fruit. H. Arakawa et al. (Liebigs Ann. Chem. 728:152 [1969]) have produced 3-hydroxyadipic acid (n=2 in Formula I) by chemical methods. However, no microbiological production method is known for this compound. 3-Hydroxydodecanedioic acid (n=8 in formula I) is mentioned in the chemical synthesis of traumatic acid as an intermediate product (P. H. M. Schreurs et al., Rec. Trav. Chim. Pays-Bas 90:1331 [1971]). However, there does not as yet exist a microbiological process for the preparative production of 3-hydroxydodecanedioic acid.

Unbranched, saturated 3-hydroxydicarboxylic acids having a total of 13-18 carbon atoms are not known. In addition to those named in the examples hereinafter, others within Formula I are 3-hydroxyheptadecanedioic acid and 3-hydroxyoctadecanedioic acid.

OBJECTS OF THE INVENTION

It is an object of the invention to provide novel, unbranched, saturated 3-hydroxydicarboxylic acids of 13-18 carbon atoms. It is another object to provide a process for the preparation of unbranched, saturated 3-hydroxydicarboxylic acids of 12-18 carbon atoms. Other objects will be apparent to those skilled in the art to which this invention pertains.

Upon further study of the specification and appended claims, further objects and advantages of this invention will become apparent to those skilled in the art.

These objects are attained according to the invention by converting n-alkanes by microbial transformation into unbranched, saturated 3-hydroxydicarboxylic acids of 12-18 carbon atoms.

SUMMARY OF THE INVENTION

In a composition aspect, this invention relates to 3-hydroxydicarboxylic acids of the formula

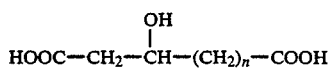

$$HOOC-CH_2-\underset{\underset{H}{|}}{\overset{\overset{OH}{|}}{C}}-(CH_2)_n-COOH \qquad (I)$$

where n is an integer from 9 to 14, and to a microbiological method for the production of the compounds of Formula I wherein n is an integer from 8 to 14.

In another composition aspect, this invention relates to *Candida tropicalis* strain DSM 3152.

In a method aspect, this invention relates to a process for the production of compounds of Formula I, which comprises preparing them from n-alkanes as the substrate by microbial transformation.

DETAILED DISCUSSION

The compounds of Formula I are produced by subjecting an n-alkane of 12-18 carbon atoms to the oxidizing activity of the strain of *Candida tropicalis*.

The microbial transformation requires a yeast mutant that can be obtained from the yeast strain *Candida tropicalis* (wild strain). After treating the wild strain with a mutations provoking substance *Candida tropicalis* DSM 3152 was selected by means of an antibiotic.

Whereas the wild strain grows in a nutrient medium made up of mineral salts and n-alkanes of 12-18 carbon atoms as the sole carbon source, the mutant *Candida tropicalis* DSM 3152 lacks this property. The differences in growth characteristics between the wild and mutant strains is shown in Table 1.

TABLE 1

| | Differences Between Wild Type and Mutant | | | | | | |
| --- | --- | --- | --- | --- | --- | --- | --- |
| | Growth on Mineral Salt and | | | | | | |
| | Glycerol | Glucose | Dodecane | Tridecane | Tetradecane | Pentadecane | Hexadecane |
| *Candida tropicalis* (Wild Strain) | ++ | +++ | ++ | ++ | ++ | ++ | +(+) |
| Mutant DSM 3152 | ++ | +++ | − | − | − | − | − |

− = no growth
+ = satisfactory growth
++ = good growth
+++ = good growth

*Candida tropicalis* DSM 3152 exhibits the following characteristics: Aerobic growth in glucose-yeast extractpeptone medium in the form of oval cells having a diameter of 2-6 um. Aerobic growth in a mineral nutrient solution with addition of vitamins and the carbon sources glycerol, ethanol, succinic acid or D-glucose. Satisfactory growth after addition of D-biotin. No growth in a mineral nutrient solution with addition of n-alkanes of 12-18 carbon atoms (not even after adding emulsifiers). (For this reason, this microorganism is called "alkanebreakdown-defective" mutant.) Under satisfactory growth conditions, n-alkanes of 12-18 carbon atoms are converted into 3-hydroxydicarboxylic acids having the same number of carbon atoms.

To obtain satisfactory growth, the nutrient medium employed desirably contains: inorganic salts of cations such as ammonium, potassium, sodium, calcium, magnesium, manganese, iron, and the anions phosphate, nitrate, chloride, sulfate and carbonate; organic nutrients of a simple constitution, such as ethanol, glycerol, acetic acid and glucose; organic nutrients of a complex constitution, such as yeast extract, corn steep liquor, and peptones from vegatable and/or animal proteins.

Additional requirements for satisfactory growth are: a temperature of about 20°-40° C.; pH of about 3-8; aeration of the culture broth of yeast and nutrient medium.

The n-alkane to be converted can be added to the culture broth all at once, in individual portions, or continuously. Emulsifiers can also be added to accelerate the conversion of the n-alkanes. Especially useful are polyglycol ethers of fatty alcohols known under the trade name BRIJ[R]. They will be added to the culture media in a concentration of 0.05-0.5%.

Since the pH value of the batch drops during fermentation as a result of the formation of acids, bases can be added in metered quantities to maintain the pH within the desired range. Customary bases are ammonia, sodium hydroxide solution, potassium hydroxide solution, or calcium hydroxide.

The oxygen needed for converting the n-alkanes into 3-hydroxydicarboxylic acids is introduced by aerating the culture broth with air or with oxygen-enriched air. Conventional submerged fermentation conditions can be employed.

After fermentation is completed, the 3-hydroxydicarboxylic acids can be separated and purified according to conventional methods. Suitable are precipitation, extraction, ion-exchange chromatography, and electrodialysis.

A preferred method for the production of the 3-hydroxydicarboxylic acids in pure form employs the following steps:

1. The culture broth is adjusted to pH>8.
2. Yeast biomass and unreacted n-alkanes are separated by centrifuging.
3. The 3-hydroxydicarboxylic acids and other products containing carboxy groups are precipitated by acidifying the solution of pH<5.
4. The thus-precipitated products are separated, washed, dried and then esterified, e.g., with methanol.
5. The thus-produced esters, e.g., dimethyl esters, of the 3-hydroxydicarboxylic acids are chromatographically separated and purified.
6. Alkaline saponification yields the corresponding 3-hydroxydicarboxylic acids.

After esterification the purification of the diester of the 3-hydroxydicarboxylic acid from contaminating diesters of dicarboxylic acids is easily done by chromatography with an apolar solvent and silica powder, for differences in retention behavior are enhanced by esterification.

n-Alkane conversions of 50% or more can be achieved according to the process of this invention. Alkanedicarboxylic acids are sometimes the predominant conversion product. However, even more than 50% of the conversion products are 3-hydroxydicarboxylic acids under some conditions, especially when long chain n-alkanes like n-hexadecane are used as a substrate.

The parts of 3-hydroxydicarboxylic acids and dicarboxylic acids can readily be determined by gas chromatography analysis.

The process of this invention makes possible the direct production of 3-hydroxydicarboxylic acids of 12-18 carbon atoms from n-alkanes by a simple method under gentle conditions.

The 3-hydroxydicarboxylic acids produced according to this invention are useful as starting materials for synthetic polymers, fragrances, tensides, emulsifiers and bleaching agents. In the latter case the 3-hydroxydioic acids are reacted with hydrogenperoxide in sulfuric acid to form the corresponding diperoxydioic acids, which can be used as effective bleaching agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

A nutrient solution with substrate is prepared, containing per liter

| | |
|---|---|
| 3 g | $NH_4NO_3$ |
| 3 g | $(NH_4)_2SO_4$ |
| 1.5 g | $KH_2PO_4$ |
| 1 g | $K_2HPO_4$ |
| 6 g | corn steep liquor |
| 0.2 g | KCl |
| 4 mg | $FeSO_4.7H_2O$ |
| 0.4 mg | $ZnSO_4.7H_2O$ |
| 1 mg | $MnSO_4.H_2O$ |
| 10 g | glycerol |
| 2 g | emulsifier ("BRIJ" 35) |
| 6 g | n-dodecane |

500 ml of this solution is inoculated with the yeast strain DSM 3152 and then aerobic incubation is effected for 3 days at 30° C. With the 500 ml of the thus-formed subculture, 5 l of a solution having the above composition is then inoculated in a 10 liter fermentor. The 5.5 l batch is stirred at 30° C. and 600 rpm and aerated with 1 liter of air per liter of reactor volume and minute (1 vvm).

The pH value is maintained at pH 6.0 by adding 8N NaOH. After 20 hours, feeding of 1 l of n-dodecane and 600 ml of 10% ammonium acetate solution is begun; per hour, 20 ml of n-dodecane and 12 ml of ammonium acetate solution are introduced in metered quantities into the fermentor. At the same time, the pH value of the reaction batch is raised from pH 6.0 to pH 7.5. After 90 hours of operation, the fermentation is finished and the batch is worked up.

For this purpose, the culture broth is adjusted to pH 9 and the biomass and residual n-dodecane are separated by centrifuging. The thus-formed long-chain di acids are precipitated by acidifying with hydrochloric acid to pH 3 and obtained by washing and drying in the crude form as a product mixture. Yield: 210 g.

Analysis by gas chromatography (Table 2) shows that 5% 3-hydroxydodecanedioic acid is present in the product mixture.

TABLE 2

Gas Chromatography Analysis of the Di Acids Prepared from n-Dodecane

| Acid Identified | Content Weight-% |
|---|---|
| Decanedioic Acid | 2.2 |
| Undecanedioic Acid | 0.3 |
| Dodecanedioic Acid | 91.3 |
| 3-Hydroxydecanedioic Acid | 0.7 |
| 3-Hydroxyundecanedioic Acid | 0.1 |
| 3-Hydroxydodecanedioic Acid | 5.0 |
| | 99.6 |

Example 2

The procedure of Example 1 is repeated, but with the use of n-tridecane in place of n-dodecane as the substrate.

Precipitated and dried di acids in the amount of 550 g are obtained as the product mixture. The analysis by gas chromatography shows that this mixture contains 9% 3-hydroxytridecanedioic acid (Table 3).

TABLE 3

| Gas Chromatography Analysis of the Di Acids Prepared from n-Tridecane | |
|---|---|
| Acid Identified | Content Weight-% |
| Undecanedioic Acid | 1.0 |
| Dodecanedioic Acid | 0.2 |
| Tridecanedioic Acid | 84.4 |
| 3-Hydroxyundecanedioic Acid | 0.6 |
| 3-Hydroxydodecanedioic Acid | 0.7 |
| 3-Hydroxytridecanedioic Acid | 9.3 |
| | 96.2 |

Example 3

The procedure of Example 1 is repeated, but using n-tetradecane in place of n-dodecane as the substrate.

As a product mixture, 430 g of precipitated and dried di acids is obtained. Analysis by gas chromatography reveals that this mixture contains 34% 3-hydroxytetradecanedioic acid (Table 4).

TABLE 4

| Gas Chromatography Analysis of the Di Acids Prepared from n-Tetradecane | |
|---|---|
| Acid Identified | Content Weight-% |
| Dodecanedioic Acid | 2.2 |
| Tridecanedioic Acid | 0.3 |
| Tetradecanedioic Acid | 47.8 |
| 3-Hydroxydodecanedioic Acid | 4.8 |
| 3-Hydroxytridecanedioic Acid | 1.0 |
| 3-Hydroxytetradecanedioic Acid | 34.0 |
| | 90.1 |

Example 4

The process is carried out as in Example 1, but with the use of n-pentadecane in place of n-dodecane as the substrate.

As a product mixture, 390 g of precipitated and dried di acids is obtained. Analysis by gas chromatography shows that this mixture contains 30% 3-hydroxypentadecanedioic acid (Table 5).

TABLE 5

| Gas Chromatography Analysis of the Di Acids Prepared from n-Pentadecane | |
|---|---|
| Acid Identified | Content Weight-% |
| Tridecanedioic Acid | 2.8 |
| Tetradecanedioic Acid | 0.9 |
| Pentadecanedioic Acid | 40.4 |
| 3-Hydroxytridecanedioic Acid | 10.1 |
| 3-Hydroxytetradecanedioic Acid | 1.2 |
| 3-Hydroxypentadecanedioic Acid | 30.4 |
| | 85.8 |

Example 5

The procedure of Example 1 is followed, but using n-hexadecane instead of n-dodecane as the substrate.

A product mixture of 330 g of precipitated and dried di acids is obtained. The analysis by gas chromatography reveals that this mixture contains 57% 3-hydroxyhexadecanedioic acid (Table 6).

TABLE 6

| Gas Chromatography Analysis of the Di Acids Prepared from n-Hexadecane | |
|---|---|
| Acid Identified | Content Weight-% |
| Tetradecanedioic Acid | 0.3 |
| Pentadecanedioic Acid | 0.1 |
| Hexadecanedioic Acid | 7.7 |
| 3-Hydroxytetradecanedioic Acid | 14.9 |
| 3-Hydroxypentadecanedioic Acid | 0.7 |
| 3-Hydroxyhexadecanedioic Acid | 57.0 |
| | 80.7 |

Example 6

Pure Preparation and Identification of the Dimethyl Ester of 3-Hydroxytetradecanedioic Acid The mixture of dicarboxylic acids and 3-hydroxydicarboxylic acids obtained in Example 3 is esterified with methanol under catalysis of sulfuric acid and then fractionally chromatographed on silica gel with ethyl acetate/hexane (volume ratio 1:1) as the eluent. In this step, 3-hydroxytetradecanedioic acid dimethyl ester is isolated and identified by the following analyses:

Elementary Analysis:
63.3% C (calculated: 63.6%)
10.1% H (calculated: 9.9%)
26.6% O (calculated: 26.5%)
Mass Spectrum        MW = 302
IR Spectrum:         3,400 cm$^{-1}$ (hydroxy group)
                     1,740 cm$^{-1}$ (ester)
$^{13}$C NMR Spectrum:  CDCl$_3$ as the solvent,
                     TMS as the standard

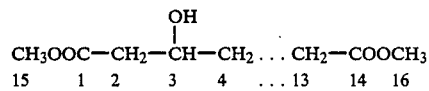

CH$_3$OOC—CH$_2$—CH—CH$_2$ ... CH$_2$—COOCH$_3$
  15       1     2     3      4  ... 13    14    16

TABLE 7

| Number of C Atom | Shift ppm | |
|---|---|---|
| 4–13 | 24.92 | |
| | 25.45 | |
| | 29.10 | (incomplete |
| | 29.20 | resolution) |
| | 29.37 | |
| | 29.46 | |
| | 34.06 | |
| 2 | 41.14 | |
| 15,16 | 51.36 | |
| | 51.64 | |
| 3 | 67.93 | |
| 1,14 | 173.25 | |
| | 174.11 | |

To isolate the free acid in pure form, the ester has to be suspended in diluted aqueous sodium hydroxid solution. After refluxing at boiling temperature the liquid is acidified with sulfuric acid. The precipitate is separated, washed with water and dried to give pure 3-hydroxytetradecanedioic acid.

The preceding examples can be repeated with similar success by substituting the generally or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. *Candida tropicalis* strain DSM 3152.

2. A process for the production of a 3-hydroxydicarboxylic acid of the formula $$\text{HOOC}-\text{CH}_2-\overset{\overset{\displaystyle \text{OH}}{|}}{\text{CH}}-(\text{CH}_2)_m-\text{COOH}$$

wherein m is an integer from 8 to 14, which comprises subjecting an n-alkane of 12–18 carbon atoms to the oxidizing activity of the strain of *Candida tropicalis* of claim 8.

3. A process according to claim 2, wherein the thus-produced dioic acids are converted to their diesters prior to purification thereof.

4. A process according to claim 3, wherein the dioic acid is 3-hydroxytetradecanedioic acid.

5. A process according to claim 3, wherein the dioic acid is 3-hydroxyhexadecanedioic acid.

6. A process according to claim 2, wherein after separating the strain of *Candida tropicalis* the thus-produced dioic acids are precipitated by acidifying the solution of pH 1–5.

* * * * *